United States Patent [19]

Sugerman et al.

[11] Patent Number: 4,634,785
[45] Date of Patent: Jan. 6, 1987

[54] TITANIUM AND ZIRCONIUM PYROPHOSPHATES, THEIR PREPARATION AND USE

[75] Inventors: Gerald Sugerman, Allendale, N.J.; Salvatore J. Monte, Staten Island, N.Y.

[73] Assignee: Kenrich Petrochemicals, Inc., Bayonne, N.J.

[21] Appl. No.: 651,119

[22] Filed: Sep. 14, 1984

[51] Int. Cl.$^4$ .............................................. C07F 7/28
[52] U.S. Cl. ...................................... 556/17; 106/299; 252/32.5; 252/49.8; 252/601; 252/609; 523/200; 523/202; 523/215; 524/28; 524/145
[58] Field of Search ........................ 260/429.3, 429.5; 556/17

[56] References Cited

U.S. PATENT DOCUMENTS

| | | | |
|---|---|---|---|
| 3,354,189 | 11/1967 | Revukas | 260/429.5 |
| 4,069,192 | 1/1978 | Monte et al. | 260/429.5 X |
| 4,087,402 | 5/1978 | Monte et al. | 260/429.5 X |
| 4,122,062 | 10/1978 | Monte et al. | 260/429.5 X |
| 4,192,792 | 3/1980 | Sugerman et al. | 260/429.5 X |
| 4,277,415 | 7/1981 | Sugerman et al. | 260/429.5 |
| 4,287,131 | 9/1981 | Langer et al. | 260/448 R |
| 4,360,474 | 11/1982 | Brady et al. | 260/429.5 |

Primary Examiner—Helen M. S. Sneed
Attorney, Agent, or Firm—Bert J. Lewen; Henry Sternberg

[57] ABSTRACT

The invention relates to a new process for producing titanium IV and zirconium IV pyrophosphates, certain of which are new compounds, and their uses. The pyrophosphates are prepared by reacting a metal tetraester with phosphorus pentoxide, with or without the addition of an hydroxyl compound, such as an alcohol or a phenol. Depending on the molar ratio of the components, the compounds produced may contain cyclic or straight chain pyrophosphate groups and alkoxy groups attached to the metallic ion. In addition to forming new compounds, the process of the invention produces the desired products without difficult-to-separate by-products. The products of the invention are useful as flame-retardants, antioxidants, coupling agents, impact modifiers and processing aids, and the reaction for their preparation may be represented as follows:

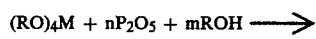

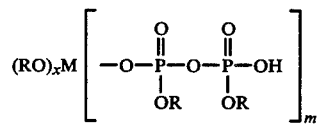

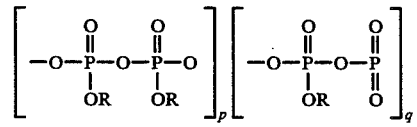

wherein M is titanium or zirconium; R is a monovalent hydrocarbon group optionally substituted with halogen or oxygen substituents; n is an integer from 1 to 4; m is an integer from 0 to 4; x is an integer from 0 to 3, and p is an integer from 0 to 2; q is an integer from 0 to 4; n is greater than or equal to m; $n = p + m + q$; $x + m + 2p + q = 4$; and when x is greater than 0, q is 0.

27 Claims, No Drawings

TITANIUM AND ZIRCONIUM PYROPHOSPHATES, THEIR PREPARATION AND USE

BACKGROUND OF THE INVENTION

Certain titanium IV pyrophosphates have been described in the literature. See U.S. Pat. No. 4,122,062. These compounds, which both have hydrolyzable and non-hydrolyzable groups, are useful as coupling agents for organic materials, such as elastomers and plastics, and particulate fillers. Conventionally, the pyrophosphaates are prepared by the condensation reaction of a dialkyl pyrophosphoric acid with a tetraalkoxy titanate whereby one mole of alcohol is liberated for each mole of the di-substituted pyrophosphoric acid reacted. Other analogous processes, such as the reaction of titanium tetrachloride with alcohol and the di-substituted pyrophosphoric acid are also feasible. Such reactions liberate hydrogen chloride.

While the foregoing organo-titanate pyrophosphates thus prepared are useful as coupling agents in many applications, the process described suffers from certain drawbacks. Firstly, the by-products generated are often difficult to separate from the desired product; and, secondly, even trace amounts of these byproducts render the pyrophosphates unsuitable for certain applications. For example, traces of hydrogen halides are inimical to basic systems and epoxy formulations, and small quantities of alcohol are detrimental to isocyanate groups.

BRIEF DESCRIPTION OF THE INVENTION

In accordance with the instant invention, a reaction scheme for preparing organo-titanate and organo-zirconate pyrophosphates is proposed which overcomes the foregoing problems. The process may also be used to prepare organo-zirconium analogs and certain new compositions of matter. The process involves the reaction of tetraalkoxy titanates or zirconates and phosphorus pentoxide with or without the addition of a hydroxyl compound such as an alcohol or phenol. For each mole of the tetraalkoxy titanate or zirconate, from 1 to 4 moles of the phosphorus pentoxide and from 0 to 4 moles of the alcohol may be added. Where from 1 to 3 moles of each the phosphorus pentoxide (n) and alcohol (m) are added to each mole of the titanate compounds and where the number of moles of the two former compounds are equal, compounds of the type described in U.S. Patent 4,122,062 are prepared. Compounds where the metal atoms are substituted solely with OP(O)(OR)OP(O)(OR)O and OP(O)(OH)OP(O)(OR)$_2$ groups, e.g. the products of the reactions C, H, and P below, are shown in U.S. Pat. No. 3,535,241. In all other instances, the organo-pyrophosphates are new compositions of matter.

The following reactions set forth the scope of reactions and reaction products contemplated in the instant invention:

| | |
|---|---|
| n = 1, m = 0 | |
| M(OR)$_4$ + P$_2$O$_5$ → <br> (RO)$_2$M[OP(O)(OR)OP(O)(OR)O] | A |
| n = 1, m = 1 | |
| M(OR)$_4$ + P$_2$O$_5$ + HOR → <br> (RO)$_3$M[OP(O)(OH)OP(O)(OR)$_2$] | B |
| n = 2, m = 0 | |
| M(OR)$_4$ + 2P$_2$O$_5$ → <br> M[OP(O)(OR)OP(O)(OR)O]$_2$ | C |
| n = 2, m = 1 | |
| M(OR)$_4$ + 2P$_2$O$_5$ + HOR → <br> (RO)M[OP(O)(OH)OP(O)(OR)$_2$] [OP(O)(OR)OP(O)(OR)O] | D |
| n = 2, m = 2 | |
| M(OR)$_4$ + 2P$_2$O$_5$ + 2HOR → <br> (RO)$_2$M[OP(O)(OH)OP(O)(OR)$_2$]$_2$ | E |
| n = 3, m = 0 | |
| M(OR)$_4$ + 3P$_2$O$_5$ → <br> M[OP(O)(OR)OP(O)(OR)O] [OP(O)(OR)OP(O)$_2$]$_2$ | F |
| n = 3, m = 1 | |
| M(OR)$_4$ + 3P$_2$O$_5$ + HOR → <br> M[OP(O)(OH)OP(O)(OR)$_2$] [OP(O)(OR)OP(O)(OR)O] [OP(O)(OR)OP(O)$_2$] | G |
| n = 3, m = 2 | |
| M(OR)$_4$ + 3P$_2$O$_5$ + 2HOR → <br> M[OP(O)(OH)OP(O)(OR)$_2$]$_2$ [OP(O)(OR)OP(O)(OR)O] | H |
| n = 3, m = 3 | |
| M(OR)$_4$ + 3P$_2$O$_5$ + 3HOR → <br> (RO) M[OP(O)(OH)OP(O)(OR)$_2$]$_3$ | J |
| n = 4, m = 0 | |
| M(OR)$_4$ + 4P$_2$O$_5$ → <br> M[OP(O)(OR)OP(O)$_2$]$_4$ | K |
| n = 4, m = 1 | |
| M(OR)$_4$ + 4P$_2$O$_5$ + HOR → <br> M[OP(O)(OH)OP(O)(OR)$_2$] [OP(O)(OR)OP(O)$_2$]$_3$ | L |
| n = 4, m = 2 | |
| M(OR)$_4$ + 4P$_2$O$_5$ + 2HOR → <br> M[OP(O)(OH)OP(O)(OR)$_2$]$_2$ [OP(O)(OR)OP(O)$_2$]$_2$ | M |
| n = 4, m = 3 | |
| M(OR)$_4$ + 4P$_2$O$_5$ + 3HOR → <br> M[OP(O)(OH)OP(O)(OR)$_2$]$_3$ [OP(O)OP(O)$_2$] | N |
| n = 4, m = 4 | |
| M(OR)$_4$ + 4P$_2$O$_5$ + 4HOR → <br> M[OP(O)(OH)OP(O)(OR)$_2$]$_4$ | P |

The reactions B, E and J represent the formation of compounds shown in the aforementioned U.S. Patent. It will be understood that, while pyrophosphate moieties are represented as having two organo substituted groups on a specific phosphorus atom, such moieties are in equilibrium with di-substituted pyrophosphate moieties having one organo-substituent on each of the phosphorus atoms.

As will be seen from the above reactions, no by-products are formed in the process of the instant invention. Accordingly, there is no need to separate by-products and the problems caused by by-product residue do not occur.

DETAILS OF THE INVENTION

The products and the process of the subject invention may be represented as follows:

$$(RO)_4M + nP_2O_5 + mROH \longrightarrow$$

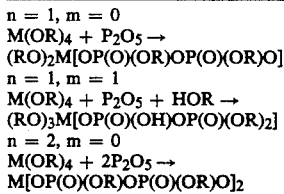

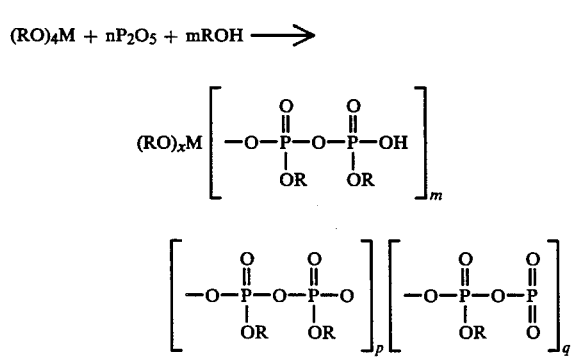

wherein M is titanium or zirconium; R is a monovalent hydrocarbon group optionally substituted with halogen or oxygen substituents; n (the number of moles of phosphorus pentoxide) is an integer from 1 to 4; m (the number of moles of alcohol reacted and the number of disubstituted straight-chain pyrophosphate groups per mole) is an integer from 0 to 4; x (the number of alkoxy groups per mole) is an integer from 0 to 3; p (the number of divalent disubstituted pyrophosphate groups per mole) is an integer from 0 to 2; q (the number of monosubstituted pyrophosphate groups) is an integer from 0 to 4; n is greater than or equal to m; $n = p + m + q$; $x + m + 2p + q = 4$; and when x is greater than 0, q is 0.

The R groups may contain from 1 to 30 carbon atoms and are preferably alkyl, alkenyl, alkynyl and aralkyl, aryl and alkaryl groups.

Examples of preferred products are as follows:

TABLE A

| Product Designation | Chemical Structure |
|---|---|
| AT1 | $(C_8H_{17}O)_2Ti[OP(O)(OC_8H_{17})OP(O)(OC_8H_{17})O]$ |
| AZ1 | $(C_6H_5O)_2Zr[OP(O)(OC_4H_9)OP(O)(OCH_2C_6H_5)O]$ |
| CT1 | $Ti[OP(O)(OCH_2OC_2H_5)OP(O)(OCH_2OC_2H_5)O]_2$ |
| DT1 | $(C_6H_{11}O)Ti[OP(O)(OH)OP(O)(OR^1)(OR^2)] [OP(O)(OR^1)OP(O)(OR^1O]$ wherein $R^1 = C_4H_9$ and $R^2 = C_2H_5$ |
| FT1 | $Ti[OP(O)(OCH_2CHBrCH_2Br)OP(O)(OCH_2CHBrCH_2Br)O]$ $[OP(O)(OCH_2CHBrCH_2Br)OP(O_2)]_2$ |
| FZ1 | $Zr[OP(O)(OC_{10}H_6OCH_3)OP(O)(OC_{10}H_6OCH_3)O] (OP(O)(OC_{10}H_{16}OCH_3)OP(O)_2]_2$ |
| FZ2 | $Zr[OP(O)(OC_3H_7)OP(O)(OC_3H_7)O] [OP(O)(OC_3H_7)OP(O)_2]_2$ |
| GT1 | $Ti[OP(O)(OH)OP(O)((OC_6H_3(CH_3)_2))_2]$ $[OP(O)((OC_6H_3)_2))OP(O)((OC_6H_3(CH_2)_2))O] [OP(O)((OC_6H_3(CH_3)_2))OP(O)_2]$ |
| HZ1 | $Zr[OP(O)(OH)OP(O)(OR^3)_2] [OP(O)(OR^3)OP(O)(OR^3)O]$ wherein three $R^3$s are butyl and two $R^3$s are octyl with random distribution of the various isomers. |
| KT1 | $Ti[OP(O)(OC_5H_{11})OP(O)_2]_4$ |
| KZ1 | $Zr[OP(O)((OC_6H_4C(CH_3)_2C_6H_5))OP(O)_3]_4$ |
| KT2 | $Ti[OP(O)(OCH_2CH=CH_2)OP(O)_2]_3 [OP(O)(OC_6H_5)OP(O)_2]$ |
| LT1 | $Ti[OP(O)(OC_8H_{17})OP(O)(OH)(OC_8H_{17})] [OP(O)(OC_8H_{17})OP(O)_2]_3$ |
| MZ1 | $Zr[OP(O)(OC_5H_5)OP(O)(OH)(OC_5H_5)_2 [OP(O)(OC_5H_5)OP(O)_2]_2$ |
| NT1 | $Ti[OP(O)(OH)OP(O)(OC_3H_7)_2]_3 [OP(O)(OC_6H_4CH_3)OP(O)_2]$ |
| PT1 | $Ti[OP(O)(OH)OP(O)(OC_2H_4OC_2H_4OC_6H_5)_2]_4$ |
| PT2 | $Ti[OP(O)(OH)OP(O)(O-n-C_{18}H_{33})_2]_4$ |
| PZ3 | $Zr[OP(O)(OH)OP(O)(OCH_2-2-C_4H_3O)_2]_4$ |

The compositions of the invention find their primary applications in chemical and physical admixtures with polymeric material. For example, where the metallo-organic pyrophosphate if formed by reacting the metallic ester solely with phosphorus pentoxide, the following applications have been demonstrated (the numbers in parentheses indicating the percent of the pyrophosphates used in the polymer, based on the total weight of the admixture: antioxidant (0.01 to 1%); polymerization initiators (0.01 to 1%); anticorrosive agents (0.1 to 1%); processing aids (0.1 to 1%); coupling agents (0.01 to 1%); and impact modifiers (0.1 to 3%). Where the pyrophosphate is the reaction product of all three components, the compounds of the invention are outstanding flame-retardants. Here from 0.5 to 5% by weight of the materials are used.

Since these compounds have active protons and function as Bronsted acids, they may be reacted with bases to form water-soluble salts. Such salts are particularly useful as flame-retardants for flammable compositions which are dispersed in aqueous media, e.g., a water-dispersible acrylic paint. In addition, they improve the physical properties of the paint, thereby improving surface adhesion and, desirably, the hydrophobic nature of the paint layer. Monoammonium phosphate, the prior art additive used to enhance flame retardance, on the other hand, is hydrophilic, and therefore tends to increase the moisture absorption of the paint.

Still other applications of the compounds of the instant invention are as dehydrating agents in resins. They may be used in amounts of from 0.1 to 3%. In those instances where the number of moles of phosphorus pentoxide reacted is greater than the number of moles of alcohol, the compounds of the invention may be used as co-monomers to form polymers having phosphorus linkages in their backbone. Co-polymerization with isocyanates is an example of such application and from 0.5 to 25 wt.% of the pyrophosphate may be used. Those compounds having cyclic rings are useful for enhancing conductivity.

In those pyrophosphates prepared by reacting at least 3 moles of the phosphorus pentoxide with each mole of the organo-metallic compound, it will be noted that the organic constituents in the product are comparatively small in relationship to the total molecular weight. This low organic content, makes these materials suitable for high temperature applications, such as required for soldering and welding fluxes, and for dissolving metallic oxides.

In the two-reactant system where 3 or 4 moles of the phosphorus pentoxide are reacted, the compounds produced can be used for the formation of liquid ceramics. Such materials are thermally stable at temperatures of 550° C. and insoluble in aromatic and aliphatic solvents.

The reactions of the instant invention are readily performed and post no difficulty for those skilled in the art. Where only the organo-metallic compound and the phosphorus pentoxide is reacted, the reaction may be readily performed in aromatic hydrocarbons, e.g., benzene, alkyl naphthylenes, toluene, xylene, tetrahydronaphthene, methyl and dimethyl naphthene, tetrahydrofuran and anisol; or ethers, e.g., methyl phenyl ether or diethyl ether. The amount of solvent is not critical; as little as 10% and up to 95% of solvent may be added, based on the amount of reaction products. The temperature of the reaction may be from 25° to 250° C., preferably from 40° to 120° C. Certain solvents should clearly be avoided, such as aprotic solvents or solvents having ester groups or active double bonds.

In the case of the three-reactant process, extraneous solvents need not be added, since the alcohol or phenol may be used to dissolve the other reactants. On the other hand, solvents such as aromatics, ethers, or chlorinated paraffins may be used. So long as the reactants remain in the liquid state, the temperature is not particularly critical. Accordingly, temperatures as low as −10° C. and as high as 180° C. or greater may be employed.

Where the compounds prepared in accordance with the instant invention have both hydrophobic and hydrophilic groups attached to the metallic atom, the compositions may be used as coupling agents. Such applications are taught in U.S. Pat. No. 4,122,062, the disclosure of which is incorporated herein by reference.

In order to more fully describe the instant invention, attention is directed to the following examples:

from the indicated solvent to provide a product suitable for analytical evaluation. In certain instances, the crude still bottoms and the undistilled crude reaction mixture was suitable for many applications. Specifics are given in Table 1. Note that reverse addition, i.e., the addition of metallic tetraester to slurried phosphorous pentoxide, gave comparable yields in the cases of $(C_8H_{17}O)_4$ Ti and $(C_3H_7O)_4$ Zr conversion examples. This example illustrates Reaction A.

TABLE 1

| Metallic Tetraester | Reaction Solvent | Reaction Temp. °C. | Recrystallization Solvent | Product | Yield Mole % | mp °C. | Calc % P Found % P |
|---|---|---|---|---|---|---|---|
| $(C_8H_{17}O)_4Ti$ | Xylene 4:1 | 35–94 | Cyclohexane | $(C_8H_{17}O)_2Ti[OP(O)(OC_8H_{17})OP(O)(OC_8H_{17})O]$ | 79 | 78–82 | 8.78 / 8.83 |
| $(CH_3OC_2H_4O)_4Ti$ | None | 21–152 | $CCl_4$ | $(CH_3OC_2H_4O)_2Ti[OP(O)(OC_2H_4OCH_3)OP(O)(OC_2H_4OCH_3)O]$ | 64 | 61–66 | 12.65 / 12.58 |
| $(C_6H_5O)_2(CH_3O)_2Ti$ | $(CH_3OCH_2)_2$ 1:1 | 19–38 | Heptane | $(C_6H_5O)_2Ti[OP(O)(OCH_3)OP(O)(OCH_3)O]$ | 87 | 101–103 | 14.16 / 14.08 |
| $(CH_2=CHCH_2OCH_2)_2(C_2H_5)CCH_2OTi(OCH_2C_6H_5)_3$ | None | 24–131 | Xylene | $(CH_2=CHCH_2OCH_2)_2(C_2H_5)CCH_2OTi(OCH_2C_6H_5)[OP(O)(OCH_2C_6H_5)OP(O)((OCH_2C_6H_5)O]$ | 59 | 133–137 | 8.56 / 8.61 |
| $(C_3H_7O)_4Zr$ | Methyl cyclohexane 0.5:1 | 27–65 | Xylene | $(C_3H_7O)_2Zr[OP(O)(OC_3H_7)OP(O)(OC_3H_7)O]$ | 68 | 106–109 | 13.22 / 13.16 |
| $(C_3H_5O)_4Zr$ | Methyl cyclohexane 4:1 | 21–80 | Cyclohexane | $(C_3H_5O)_2Zr[OP(O)(OC_3H_5)OP(O)(OC_3H_5)O]$ | 81 | 89–93 | 13.05 / 12.96 |

EXAMPLE 1

Dialkoxy/aroxy, mono(diester)cyclopyrophosphato-O, O salts of titanium IV/zirconium IV One mole of a tetra (alkoxy/aroxy) titanium IV or zirconium IV salt, optionally with an inert reaction solvent, was placed in a corrosion resistant, power mixed and (external) temperature controlled reaction vessel. Where the solvent was used the ratio represents the weight ratio of solvent to the metallic salt. One mole of phosphorous pentoxide powder was added at a rate such that the reaction mix temperature stayed within the limits specified in Table 1 below. Where solvent was employed, the resulting solution was vacuum distilled to give a bottoms bp at 5 mm Hg equal to or greater than 100° C. The still residue (or the crude product where no solvent was used) was then recrystallized

EXAMPLE 2

Tri(alkoxy/aroxy)mono(diester)pyrophosphato-O, salts of titanium IV and zirconium IV Example 1 was repeated except that one mole of the indicated alcohol or phenol (ROH) was added to the metallic tetraester prior to phosphorus pentoxide addition. These are examples of Reaction B. Specifics are given in Table 2.

TABLE 2

| Metallic Tetraester | Reaction Solvent | ROH | Reaction Temp. °C. | Recrystallization Solvent | Product | Yield Mole % | mp °C. | Calc % P | Found % P |
|---|---|---|---|---|---|---|---|---|---|
| $(iC_3H_7O)_4Ti$ | None | $iC_3H_7OH$ | 17–82 | Hexane | $i(C_3H_7O)_3Ti[OP(O)(OA)OP(O)(OB)(OC)]$ wherein A,B,C = (H), $i(C_3H_7)$, $(iC_3H_7)$ | 72 | 62–65 | 12.78 | 12.59 |
| $(ClC_6H_4O)_4Ti$ | Xylene 3:1 | $C_4H_9OH$ | 68–104 | Toluene | $(ClC_6H_4O)_3Ti[OP(O)(OA)OP(O)(B)(C)]$ wherein A,B,C, = (OH), $(OC_4H_9)$, $(OC_6H_4Cl)$ | 81 | 81–88 | 8.01 | 7.92 |
| $(C_6H_{11}O)_4Zr$ | Xylene 4:1 | $C_6H_{11}OH$ | 22–75 | $(CH_3OCH_2)_2$ | $(C_6H_{11}O)_3Zr[OP(O)(OA)OP(O)(OB)(OC)]$ wherein A,B,C = (OH), $(C_6H_{11})$, $(C_6H_{11})$ | 63 | 58–63 | 8.52 | 8.59 |

EXAMPLE 3

Titanium IV and zirconium IV bis-cyclo(diester)pyrophosphato-O, O Salts

The process of Example 1 was repeated except that the ratio of phosphorus pentoxide to metallic ester was increased from equimolar to two to one. This is Reaction C. Specifics are given in Table 3.

TABLE 3

| Metallic Tetraester | Reaction Solvent | Reaction Temp. °C. | Recrystallization Solvent | Product | Yield Mole % | mp °C. | Calc % P | Found % P |
|---|---|---|---|---|---|---|---|---|
| $(C_5H_9O)_4Ti$ | $(CH_3OCH_2)_2$ 4:1 | 30–65 | Methyl cyclohexane | $Ti[OP(O)(OC_5H_9)OP(O)(OC_5H_9)O]_2$ | 67 | 141–145 | 18.45 | 18.27 |

TABLE 3-continued

| Metallic Tetraester | Reaction Solvent | Reaction Temp. °C. | Recrystal- ization Solvent | Product | Yield Mole % | mp °C. | Calc % P | Found % P |
|---|---|---|---|---|---|---|---|---|
| [(CH$_3$)$_2$C$_6$H$_3$O]$_4$Ti | C$_{10}$H$_7$CH$_3$ 4:1 | 75-120 | CCl$_4$ | Ti[OP(O)((OC$_6$H$_3$(CH$_3$)$_2$)OP(O) ((OC$_6$H$_3$(CH$_3$)$_2$))O]$_2$ | 54 | 172-179 | 15.20 | 15.07 |
| (C$_6$H$_5$CH$_2$O)$_4$Zr* | C$_{10}$H$_7$CH$_3$ 1:1 | 60-125 | CCl$_4$ | Zr[OP(O)(OCH$_2$C$_6$H$_5$)OP(O) (OCH$_2$C$_6$H$_5$)O]$_2$ | 63 | 79-82 | 15.44 | 15.36 |
| (C$_8$H$_{17}$O)$_4$Zr | Xylene 3:1 | 21-84 | Hexane | Zr[OP(O)(OC$_8$H$_{17}$OP(O) (OC$_8$H$_{17}$)O]$_2$ | 80 | 96-99 | 13.92 | 14.04 |

*Reverse addition (zirconate to P$_2$O$_5$ slurry) gave a comparable product in 74% yield.

EXAMPLE 4

Alkoxy/aroxy, cyclo(diester)pyrophosphato-O,O,diester pyrophosphato-O Salts of titanium IV and zirconium IV The process of Example 1 was repeated except that one mole of an alcohol or phenol (ROH) was added to the metallic tetraester prior to phosphorus pentoxide introduction and the ratio of phosphorus pentoxide to metallic tetraester was doubled. These examples show Reaction D. Specifics are given in Table No. 4.

TABLE 4

| Metallic Tetraester | Reaction Solvent | ROH | Reaction Temp. °C. | Recrystal- ization Solvent | Product | Yield Mole % | mp °C. | Calc % P | Found % P |
|---|---|---|---|---|---|---|---|---|---|
| (Br$_2$C$_6$H$_3$O)$_4$Ti | Xylene 4:1 | Br$_2$C$_6$H$_3$OH | 65-105 | CCl$_4$ | Br$_2$C$_6$H$_3$OTi[OP(O)(OA)OP (O)(OB)OC][OP(O)(OC$_6$H$_3$Br$_2$) O] where A,B,C, = (H), (C$_6$H$_3$Br$_2$), (C$_6$H$_3$Br$_2$) | 57 | 138-141 | 7.86 | 7.81 |
| (C$_8$H$_{17}$O)$_4$Ti | None | C$_8$H$_{17}$OH | 30-45 | Cyclo- hexane | (C$_8$H$_{17}$O)Ti[OP(O)(OA)OP (OB)(OC)][OP(O)(OC$_8$H$_{17}$)O] where A,B,C, = (H), (C$_8$H$_{17}$) (C$_8$H$_{17}$) | 68 | 79-82 | 12.69 | 12.46 |
| (C$_3$H$_7$O)$_4$Zr* | None | C$_6$H$_5$—OH | 75-140 | Hexane | C$_6$H$_5$OZr[OP(O)(OA)OP(O) (OB)OC)][OP(O)(OC$_3$H$_7$)OP (O)(OC$_3$H$_7$)O] where A,B,C, = (H), (C$_3$H$_7$),(C$_3$H$_7$) | 74 | 92-96 | 17.59 | 17.46 |

*Post addition of the phenol to the reaction product of two moles of phosphorus pentoxide (suspended in 3:1 diglyme) with one mole of zirconium IV tetrakis-propanolato at 60-150° C. followed by evaporation of reaction solvent and recrystallization of the residue from methyl chloroform gave a comparable product (IR analysis), m.p. 93-96° C., in 81 mole percent yield.

EXAMPLE 5

Titanium IV and zirconium IV bis alkylato/arylato, bis(diester)pyrophosphato-O

The process described in Example 1 was repeated except that two moles of alcohol/phenol per mole of metallic ester were added prior to the addition of two moles of phosphorus pentoxide. This illustrates Reaction E.

TABLE 5

| Metallic Tetraester | Reaction Solvent | ROH | Reaction Temp. °C. | Recrystal- ization Solvent | Product | Yield Mole % | mp °C. | Calc % P | Found % P |
|---|---|---|---|---|---|---|---|---|---|
| (C$_4$H$_9$O)$_4$Ti | None | C$_4$H$_9$OH | 21-40 | Hexane | (C$_4$H$_9$O)$_2$Ti[OP(O)(OA)OP(O) (OB)OC]$_2$ where A,B,C, = (H), (C$_4$H$_9$),(C$_4$H$_9$) | 69 | 59-61 | 16.08 | 16.23 |
| (C$_{10}$H$_7$O)$_4$Ti | Xylene 4:1 | C$_6$H$_{13}$OH | 38-55 | CCl$_4$ | (C$_{10}$H$_7$O)$_2$Ti[OP(O)(OA)OP(O) (OB(OC)]$_2$ where A,B,C, = (H), (C$_6$H$_{13}$)(C$_{10}$H$_7$) | 53 | 102-107 | 12.33 | 12.09 |
| (C$_8$H$_{17}$O)$_4$Zr | None | C$_4$H$_9$OH, C$_6$H$_3$(CH$_3$)$_3$ OH | 22-48 | CCl$_4$ | (C$_6$H$_3$(CH$_3$)$_2$O)(OD)Zr[OP(O)(OA) OP(O)(OB)(OC)]$_2$ where A,B,C,D, = (H),(C$_4$H$_9$),(C$_8$H$_{17}$),(C$_8$H$_{17}$) provided D $\neq$ (H) | 57 | 89-93 | 11.41 | 11.58 |

EXAMPLE 6

Titanium IV and zirconium IV bis(monoester)pyrophosphato-O, cyclo(diester)pyrophosphato-O,O The process described in Example 1 was repeated except that the ratio of phosphorus pentoxide to metallic ester was increased to 3:1. These runs exemplify Reaction F.

TABLE 6

| Metallic Tetraester | Reaction Solvent | Reaction Temp. °C. | Recrystal- ization Solvent | Product | Yield Mole % | mp °C. | Calc % P | Found % P |
|---|---|---|---|---|---|---|---|---|
| (C$_8$H$_{17}$O)$_4$Ti | Xylene 4:1 | 20-85 | CCl$_4$ | Ti[OP(O)(OC$_8$H$_{17}$)OP(O)]$_2$ [OP(O)(OC$_8$H$_{17}$)OP(O) | 82 | 121-124 | 17.94 | 18.03 |

TABLE 6-continued

| Metallic Tetraester | Reaction Solvent | Reaction Temp. °C. | Recrystal- ization Solvent | Product | Yield Mole % | mp °C. | Calc % P | Found % P |
| --- | --- | --- | --- | --- | --- | --- | --- | --- |
| [(CH$_3$)(Cl)(C$_6$H$_3$O)]$_4$Ti | Toluene 3:1 | 45–70 | Cyclohexane | (OC$_8$H$_{17}$)O] Ti[OP(O)((OC$_6$H$_3$(CH$_3$)(Cl))) OP(O)$_2$] [OP(O)((OC$_6$H$_3$(Cl) (CH$_3$)OP(O)((OC$_6$H$_3$)))O] | 51 | 78–83 | 17.88 | 17.79 |
| (CH$_3$OC$_2$H$_4$O)$_4$Zr | CCl$_4$ 6:1 | 28–60 | CCl$_4$ | ZrOP(O)(OC$_2$H$_4$OCH$_3$)OP(O)$_2$ OP(O)(OC$_2$H$_4$OCH$_3$)OP(O) (OC$_2$H$_4$OCH$_3$)O | 67 | 69–72 | 22.77 | 22.58 |
| (C$_3$H$_7$O)$_2$ (C$_6$H$_{11}$O)$_2$Zr | None | 65–135 | Xylene | Zr[OP(O)(OA)OP(O)$_2$]$_2$ [OP(O)(OB)OP(O)(OB)O] where A,B, = 2C$_3$H$_7$O, 2C$_6$H$_{11}$O | 58 | 121–125 | 22.33 | 22.41 |

EXAMPLE 7

Titanium IV and zirconium IV cyclo(diester)pyrophosphato-O,O diester pyrophosphato-O, monoester pyrophosphato-O The process described in Example 1 was repeated except that one mole of alcohol/phenol was added to the metallic tetraester prior to phosphorus pentoxide addition and that the mole ratio of phosphorus pentoxide to metallic ester was tripled. The runs illustrate Reaction G. Specifics are given in the Table.

EXAMPLE 8

Titanium IV and zirconium IV bis(diester)pyrophosphato-O, cyclo(monoester)pyrophosphato-O,O The process of Example 1 was repeated except that two molar equivalents of alcohol/phenol were added to the metallic ester prior to the addition of three mols of phosphorus pentoxide. These examples of Reaction H are shown in the table below.

TABLE 7

| Metallic Tetraester | Reaction Solvent | ROH | Reaction Temp. °C. | Recrystal- ization Solvent | Product | Yield Mole % | mp °C. | Calc % P | Found % P |
| --- | --- | --- | --- | --- | --- | --- | --- | --- | --- |
| (C$_3$H$_7$O)$_4$Ti | Hexane 8:1 | C$_3$H$_7$OH | 35–60 | Hexane | Ti[OP(O)(OC$_3$H$_7$)OP(O)(OC$_3$H$_7$)O] [OP(O)(OA)OP(O)(OB)OC] [OP(O)OC$_3$H$_7$)OP(O)$_2$] where A,B,C, = (H),(C$_3$H$_7$) (C$_3$H$_7$) | 62 | 134–136 | 24.19 | 24.31 |
| (C$_6$H$_5$O)$_4$Ti | Xylene 4:1 | C$_4$H$_9$OH |  | Cyclo- hexane | Ti[OP(O)(OA)OP(O)(OB)O] [OP(O)(OC)OP(O)(OD)(OE)] [OP(O)(OF)OP(O)$_2$] wherein A,B,C,D,E,F are each chosen from among (4(C$_6$H$_5$),(C$_4$H$_9$) and (H) but A,B, and F cannot be (H) | 47 | 82–87 | 20.22 | 20.16 |
| (C$_5$H$_{11}$O)$_4$Zr | Toluene 4:1 | C$_5$H$_{11}$OH | 40–90 | Methyl cyclohexane | Zr[OP(O)(OC$_5$H$_{11}$)OP(O)(OC$_5$H$_{11}$)O] [OP(O)(OA)OP(O)(OB)(OC)] [OP(O)(OC$_5$H$_{11}$)OP(O)$_2$] where A,B,C, = (H),(C$_5$H$_{11}$), (C$_5$H$_{11}$) | 72 | 111–115 | 19.54 | 19.39 |

TABLE 8

| Metallic Tetraester | Reaction Solvent | ROH | Reaction Temp. °C. | Recrystal- ization Solvent | Product | Yield Mole % | mp °C. | Calc % P | Found % P |
| --- | --- | --- | --- | --- | --- | --- | --- | --- | --- |
| (C$_6$H$_5$CH$_2$O)$_4$Ti | Xylene 8:1 | CH$_3$OH C$_4$H$_9$OH | 60–75 | Hexane | Ti[OP(O)(OA)OP(O)(OB)O] [OP(OC)OP(O)(OD)(OE)]$_2$ where A,B,C,D,E = 4(C$_6$H$_5$CH$_2$),(CH$_3$),(C$_4$H$_9$),(H), provided A and B are not both (H) | 54 | 93–97 | 18.45 | 18.42 |
| (C$_8$H$_{17}$O)$_4$Ti | CCl$_4$ 8:1 | C$_8$H$_{17}$OH | 55–70 | CCl$_4$ | Ti[OP(O)(OC$_8$H$_{17}$)O] [OP(O)(OA)OP(O)(OB)(OC)]$_2$ where A,B,C = (C$_8$H$_{17}$),(C$_8$H$_{17}$), (H) | 61 | 105–108 | 14.90 | 15.03 |
| (C$_3$H$_7$O)$_4$Zr | Toluene 10:1 | C$_3$H$_7$OH | 40–85 | CCl$_4$ | Zr[OP(O)(OC$_3$H$_7$)OP(O)(OC$_3$H$_7$)O] [OP(O)(OA)OP(O)(OB)(OC)]$_2$ where A,B,C = (C$_3$H$_7$),(C$_3$H$_7$),(H) |  |  | 22.91 | 22.79 |

EXAMPLE 9

Mono alkoxy/aroxy tris(diester)pyrophosphato-O salts of titanium IV and zirconium IV The process of Example 1 was repeated except that three moles of alcohol per mol of metallic ester were added prior to the addition of three moles of phosphorus pentoxide. The table below shows Reaction J.

EXAMPLE 11

The utility of the products of the invention as flame retardants is shown in this example. Aluminum foil strips measuring 20 cm×1 cm×0.05 cm were hung vertically and simultaneously coated on both sides with 0.2 mm of a 10% glyme solution of the indicated product. After coating, the vertical strips were oven dried in

TABLE 9

| Metallic Tetraester | Reaction Solvent | ROH | Reaction Temp. °C. | Recrystalization Solvent | Product | Yield Mole % | mp °C. | Calc % P | Found % P |
|---|---|---|---|---|---|---|---|---|---|
| $(C_3H_7O)_4Ti$ | None | $C_3H_7OH$ | 32–85 | $CCl_4$ | $(C_3H_7O)Ti[OP(O)(OB)(OC)]_3$ where A,B,C = (H),$(C_3H_7)$, $(C_3H_7)$ | 78 | 72–76 | 20.97 | 21.03 |
| $[(CH_2=CH_2OCH_2)_2 (C_2H_5)CCH_2O] (C_8H_{17}O)_3Ti$ | None | $C_8H_{17}OH$ | 22–70 | Hexane | $[(CH_2=CHCH_2OCH_2)_2(C_2H_5)CCH_2O] Ti[OP(O)(OA)OP(O)(OB)(OC)]_3$ where A,B,C = (H),$(C_8H_{17})$, $(C_8H_{17})$ | 63 | 68–71 | 15.67 | 15.91 |
| $(C_6H_5O)_4Zr$ | Xylene 4:1 | $C_4H_9OH$ | 28–65 | $CCl_4$ | $(C_6H_5O)Zr[OP(O)(OA)OP(O)(OB) (OC)]_3$ where A,B,C = (H), $(C_6H_5),(C_4H_9)$ | 71 | 104–107 | 16.74 | 16.89 |
| $(CH_3O)_4Zr$ | +-Butanol 5:1 | $CH_3OH$ | 21–60 | Xylene | $(CH_3O)Zr[OP(O)(OA)OP(O)(OB)]_3$ where A,B,C = (H),$(CH_3),(CH_3)$ | 68 | 146–148 | 25.24 | 25.09 |

EXAMPLE 10

Titanium IV and zirconium IV tetra(ester)pyrophosphato

The process of Example 1 was repeated except that four moles of phosphorus pentoxide were employed and all reactions were performed in 9:1 dilutions (based on weight of metallic ester) of diglyme. Additionally, except as otherwise noted, the indicated molar proportions of alcohol/phenol were added to the metallic ester prior to phosphorus pentoxide introduction. The first two runs illustrate Reaction K, the third run Reaction L, the fourth run Reaction M, the fifth and sixth run Reaction N, and the last two runs Reaction P.

vacuo. The dried vertical strips were evaluated for flame spread rates by bottom ignition with an oxy-acetylene torch in a fume hood. The data given represent the results from evaluating 8 to 10 samples for each product.

TABLE 11

| PRODUCT COATING | Flame Spread Rate min/15 cm |
|---|---|
| None (Control) | 12 ± 1 |
| $Ti[OP(O)(OC_3H_7)(OP(O)_2]_4$ | 47 ± 3 |
| $Ti[OP(O)(OC_5H_9)OP(O)(OC_5H_9)O]_2$ | 36 ± 2 |
| $Zr[OP(O)(OCH_2C_6H_5)OP(O)(OCH_2C_6H_5)O]_2$ | 31 ± 3 |
| $Ti[OP(O)((OC_6H_3(Cl)CH_3))OP(O)_2]_2$ $[OP(O)((OC_6H_3(Cl)(CH_3)))OP(O)((OC_6H_3(Cl)(CH_3))O]$ | 28 ± 3 |

TABLE 10

| Metallic Tetraester | ROH, moles | Reaction Temp. °C. | Recrystalization Solvent | Product | Yield Mole % | mp °C. | Calc % P | Found % P |
|---|---|---|---|---|---|---|---|---|
| $(C_8H_{17}O)_4Ti$ | None | 60–90 | Methyl naphthalene | $Ti[OP(O)(OC_8H_{17})OP(O)_2]_4$ | 73 | 181–dec | 21.9 | 22.08 |
| $(C_3H_7O)_4Zr$ | None | 55–90 | Xylene | $Zr[OP(O)(OC_3H_7)OP(O)_2]_4$ | 84 | 169–171 | 27.7 | 27.59 |
| $(C_6H_5O)_4Ti$ | $C_6H_5OH$ 1 | 60–80 | Xylene | $Ti[OP(O)(OA)OP(O)(OB)OC)]$ $[OP(O)(OC_6H_5)OP(O)_2]_3$ where A,B,C = (H), $(C_6H_5)$, $(C_6H_5)$ | 61 | 112–115 | 22.9 | 23.0 |
| $(CH_3OC_2H_4O)_4Zr$ | $CH_3OC_2H_4OH$ 2 | 50–80 | $CCl_4$ | $Zr[OP(O)(OA)OP(O)(OB)(OC)]_2$ $[OP(O)(OC_2H_4OCH_3)OP(O)_2]_2$ where A,B,C = (H),$(CH_3OC_2H_4)$, $(CH_3OC_2H_4)$ | 57 | 106–108 | 22.3 | 22.6 |
| $(C_4H_9O)_4Ti$ | $C_4H_9OH$ 3 | 30–70 | $ClC_6H_5$ | $Ti[OP(O)(OA)OP(O)(OB)(OC)]_3$ $[OP(O)(OC_4H_9)OP(O)_2]$ where A,B,C = (H),$(C_4H_9),(C_4H_9)$ | 68 | 104–109 | 21.95 | 22.04 |
| $(C_3H_7O)_4Zr$ | $C_6H_5OH$ 3 | 50–80 | Xylene | $Ti[OP(O)(OA)OP(O)(OB)(OC)]_3$ $[OP(O)(OD)OP(O)_2]$ where A,B,C,D = 3(H),4$(C_3H_7)$,3$(C_6H_5)$ but D ≠ (H) and only one of A,B,C = (H) | 43 91 | 91– | 19.5 | 19.3 |
| $(C_{18}H_{37}O)_4Ti$ | $C_{18}H_{37}OH$ 4 | 72–85 | Xylene | $Ti[OP(O)(OA)OP(O)(OB)(OC)]_4$ where A,B,C = (H),$(C_{18}H_{37})$, $(C_{18}H_{37})$ | 79 | 103–105 | 8.95 | 9.06 |
| $(C_8H_{17}O)_4Zr$ | $C_4H_9OH$ 4 | 70–85 | Xylene | $Zr[OP(O)(OA)OP(O)(OB)(OC)]_4$ where A,B,C = (H),$(C_4H_9)(C_8H_{17})$ | 60 | 97–97 | 17.3 | 17.5 |

TABLE 11-continued

| PRODUCT COATING | Flame Spread Rate min/15 cm |
|---|---|
| Zr[OP(O)(OC3H7)OP(O)(OC3H7)O]2 | 22 ± 3 |

The above data clearly show that the products of the invention are useful as flame retardants for aluminum foil.

EXAMPLE 12

This example describes the use of products of the invention as anticorrosive additives for a solvent based acrylic-urethane primer. A two part system containing the components listed below was prepared. Part A was ground in a ball mill to obtain a No. 5 Hegman grind quality. Following letdown, the coating was applied with a two nozzle spray gun, each containing one part, to a 2 mil thickness on cold rolled steel. The coatings were hardened at ambient temperature for 48 hours, after which they were scored and the coated steel subjected to salt spray (20% NaCl) at 60° C. until failure (2 mils rust). The results are given below.

TABLE 12

| Coating Composition ||||
|---|---|---|---|
| Part A ||Part B||
| Parts by wt | Component | Parts by wt | Component |
| 65 | Acrylic Resin (AU608, Rohm & Haas) | 76 | MDI Des. (N-75, Mobay) |
| 20 | Chrome Yellow (Y5775, Mobay) | 20 | Xylene (Mixed, Exxon) |
| 14 | Xylene (Mixed, Exxon) | 4 | Silica (HSTS, Cabot) |
| 1 | Zinc Naphthanate (15% Zn, Troy) | | |
| 1 | Additive (As Shown) | | |

| PRODUCT ADDITIVE | HOURS TO SALT SPRAY FAILURE |
|---|---|
| None (Control) | 108 ± 2 |
| (C8H17O)2Ti[OP(O)(OC8H17)OP(O)(OC8H17)O] | 171 ± 5 |
| Ti[OP(O)(OC6H5)OP(O)(OC6H5O)]2 | 146 ± 5 |
| Zr[OP(O)(OC3H7)OP(O)(OC3H7)O]2 | 141 ± 5 |
| Zr[OP(O)(OC4H9)OP(O)(OC4H9)][OP(O)(OA)OP(O)(OB)OC)]2 where A,B,C = (H),(C4H9),(C4H9) | 137 ± 5 |
| Zr[OP(O)(OC6H4Cl)OP(O)2]4 | 126 ± 5 |

These results clearly show that the compounds of the invention improve the anticorrosive properties of the primer.

EXAMPLE 13

This example teaches the utility of products of the invention as adhesion promoters in glass fiber reinforced thermoset polyester. Activated polyester resin (Hetron 197-3, Ashland Chem.) was admixed with 0.5 weight percent of the additive shown below. A 0.2 mil thick adhesive coating was sprayed between two sheets of 3.0 mil glass reinforced polyester resin (Aropol 7320, Ashland Chemical). The laminate was cured for 48 hours at room temperature, postcured at 100° C. for 2 hours, and allows to equilibrate at 70° F. for 24 hours. Thereafter the laminate was subjected to lap shear testing.

The results are listed in Table 13.

TABLE 13

| Additive | Lap Shear Strength, psi |
|---|---|
| Control (None) | 1430 |
| (C8H17O)2Ti[OP(O)(OC8H17)OP(O)(OC8H17)O] | 2180 |
| Zr[OP(O)(OC3H7)OP(O)(OC3H7)O]2 | 2610 |
| Zr[OP(O)(OC6H5)OP(O)2]2 [OP(O)(OC3H7)OP(O)(OC3H7)O] | 3150 |
| (C4H9O)Ti[OP(O)(OA)OP(O)(OB)(OC)]2[OP(O)(OC4H9)OP(O)(OC4H9)O] where A,B,C = (H),(C4H9),(C4H9) | 2070 |

Clearly, the above data show that the compounds of the invention act as effective adhesion promoters.

We claim:

1. An organo-metallic pyrophosphate having the following formula:

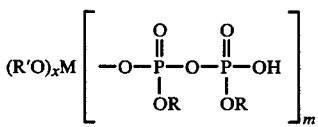

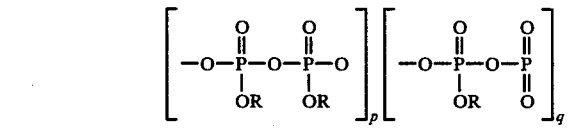

wherein R and R' are independently selected from monovalent hydrocarbon groups optionally substituted with halogen or ether oxygen substituents; M is zirconium or titanium; x+m+2p+q=4; x is an integer from 0 to 3; m and q are each integers from 0 to 4; p is an integer from 0 to 2; x+q are greater than 0; provided, however, that, when M is titanium, if x+m=4, then x=0; and, if x+m=0, then R has at least 6 carbon atoms.

2. A process for preparing organo-metallic pyrophosphates which comprises reacting an organo-metallic compound having the formula (R'O)4M with from 1 to 4 moles of phosphorus pentoxide and from 0 to 4 moles of an organic hydroxyl compound having the formula ROH, thereby forming a compound having the formula

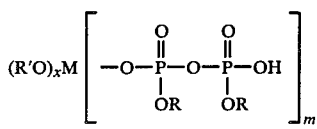

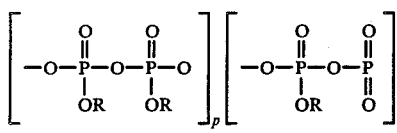

wherein R and R' are independently selected from monovalent hydrocarbon groups optionally substituted with halogen or ether oxygen substituents; M is zirconium or titanium; $x+m+2p+q=4$; x is an integer from 0 to 3; m and q are each integers from 0 to 4; p is an integer from 0 to 2; provided, however, that, when M is titanium, if $x+m=0$, then R has at least 6 carbon atoms.

3. The composition of claim 1 wherein R' is an alkyl or oxygen-substituted alkyl group having from 1 to 30 carbon atoms.

4. The composition of claim 3 wherein the R' group is isopropyl or (2,2-bis-propenolatomethyl)butanolate.

5. The composition of claim 1 wherein R is alkyl, aryl, or aralkyl wherein the alkyl groups have from 1 to 30 carbon atoms and oxygen-substituted derivatives thereof.

6. The composition of claim 5 wherein R is an alkyl group having from 1 to 8 carbon atoms, phenyl, or benzyl.

7. The composition of claim 1 wherein $x=2$ and $p=1$.

8. The composition of claim 7 wherein R and R' are octyl.

9. The composition of claim 1 where M is zirconium, $x=1$ and $m=3$.

10. The composition of claim 9 wherein R' is (2,2-bis-propenolatomethyl)butanolate and R is an alkyl group having from 1 to 8 carbon atoms.

11. The composition of claim 10 wherein R is butyl or octyl.

12. The process of claim 2 wherein R' is an alkyl or oxygen-substituted alkyl group having from 1 to 30 carbon atoms.

13. The process of claim 12 wherein the R' group is isopropyl or (2,2-bis-propenolatomethyl)butanolate.

14. The process of claim 2 wherein R is alkyl, aryl, or aralkyl wherein the alkyl groups have from 1 to 30 carbon atoms and oxygen-substituted derivatives thereof.

15. The process of claim 14 wherein R is an alkyl group having from 1 to 8 carbon atoms, phenyl, or benzyl.

16. The process of claim 2 wherein $x=2$ and $p=1$.

17. The process of claim 16 wherein R and R' are octyl.

18. The process of claim 2 where M is zirconium, $x=1$ and $m=3$.

19. The process of claim 18 wherein R' is (2,2-bis-propenolatomethyl)butanolate and R is an alkyl group having from 1 to 8 carbon atoms.

20. The process of claim 19 wherein R is butyl or octyl.

21. The process of claim 2 wherein M is titanium, $x=1$ and $m=3$.

22. The process of claim 21 wherein R is octyl and R' is isopropyl or (2,2-bis-propenolatomethyl)butanolate.

23. The process of claim 21 wherein R is a mixture of methyl and butyl and R' is isopropyl.

24. The process of claim 21 wherein R is butyl or octyl and R' is isopropyl.

25. A composition comprising a polymeric material admixed with from 0.01 to 1% of the organo-metallic pyrophosphate of claim 8.

26. A flame-retardant composition comprising a polymer and from 0.5 to 5 wt. percent of the pyrophosphate of claim 1.

27. The composition of claim 26 wherein x is 0.

* * * * *

UNITED STATES PATENT AND TRADEMARK OFFICE
CERTIFICATE OF CORRECTION

PATENT NO. : 4,634,785

DATED : January 6, 1987

INVENTOR(S) : Sugerman, Gerald & Monte, Salvatore J.

It is certified that error appears in the above-identified patent and that said Letters Patent is hereby corrected as shown below:

In claim 25, column 16, line 38, delete "claim 8" and substitute --claim 1--.

Signed and Sealed this

Twenty-fourth Day of March, 1987

Attest:

DONALD J. QUIGG

Attesting Officer

Commissioner of Patents and Trademarks